US011103365B2

(12) United States Patent
Termanini et al.

(10) Patent No.: US 11,103,365 B2
(45) Date of Patent: *Aug. 31, 2021

(54) SURGICAL TRAYS, INSTRUMENTS AND METHODS FOR REMOVING COMPONENTS OF A HIP REPLACEMENT PROSTHESIS

(71) Applicant: HIP INNOVATION TECHNOLOGY, LLC., Boca Raton, FL (US)

(72) Inventors: Zafer Termanini, Port Saint Lucie, FL (US); Brian Vanhiel, Smyrna, GA (US); Adam Ambrecht, Kennesaw, GA (US)

(73) Assignee: HIP INNOVATION TECHNOLOGY, LLC., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/917,140

(22) Filed: Jun. 30, 2020

(65) Prior Publication Data

US 2020/0330243 A1    Oct. 22, 2020

Related U.S. Application Data

(63) Continuation of application No. 15/749,380, filed as application No. PCT/US2016/047035 on Aug. 15, 2016, now Pat. No. 10,722,381.

(Continued)

(51) Int. Cl.
*A61F 2/46* (2006.01)
*A61B 50/33* (2016.01)
(Continued)

(52) U.S. Cl.
CPC ............ *A61F 2/4609* (2013.01); *A61B 50/33* (2016.02); *A61F 2/4637* (2013.01);
(Continued)

(58) Field of Classification Search
CPC ........ A61F 2/46; A61F 2/4609; A61F 2/4637; A61B 50/33
See application file for complete search history.

(56) References Cited

U.S. PATENT DOCUMENTS

| 4,729,270 A | 3/1988 | Pritchard |
| 6,565,575 B2 | 5/2003 | Lewis |

(Continued)

FOREIGN PATENT DOCUMENTS

| AU | 2006200078 B2 | 7/2006 |
| WO | 2011005191 A1 | 1/2011 |
| WO | 2015155657 A1 | 10/2015 |

OTHER PUBLICATIONS

International Search Report for corresponding application PCT/US2016/047035 dated Oct. 28, 2016.

(Continued)

*Primary Examiner* — Christopher J Beccia
(74) *Attorney, Agent, or Firm* — Norris McLaughlin PA

(57) ABSTRACT

Surgical trays and tools for use in hip revision surgery wherein the implanted prosthesis is a reverse prosthesis comprising an acetabular ball and a femoral cup. A set of trays is provided having tools for i) separating a femoral cup from an acetabular ball, ii) separating a femoral cup from a femoral implant and iii) separating an acetabular ball from an acetabular cup. A tool for removing an acetabular cup from an acetabulum is also described. A surgical method is also provided wherein the acetabular ball and femoral cup are separated first followed by, in any order, separating the femoral cup from the femoral implant and separating the acetabular ball from the acetabular cup.

20 Claims, 19 Drawing Sheets

Related U.S. Application Data

(60) Provisional application No. 62/210,652, filed on Aug. 27, 2015.

(51) Int. Cl.
*A61F 2/30* (2006.01)
*A61F 2/34* (2006.01)
*A61F 2/36* (2006.01)
*A61B 50/30* (2016.01)

(52) U.S. Cl.
CPC .................. *A61B 2050/3008* (2016.02); *A61F 2002/30332* (2013.01); *A61F 2002/30616* (2013.01); *A61F 2002/3483* (2013.01); *A61F 2002/3615* (2013.01); *A61F 2002/4619* (2013.01); *A61F 2002/4622* (2013.01); *A61F 2002/4641* (2013.01)

(56) References Cited

U.S. PATENT DOCUMENTS

| | | |
|---|---|---|
| 6,991,656 B2 | 1/2006 | Mears |
| 7,785,331 B2 | 8/2010 | Leisinger et al. |
| 8,262,667 B1 | 9/2012 | Silver et al. |
| 8,313,531 B2 | 11/2012 | Termanini |
| 8,540,779 B2 | 9/2013 | Termanini |
| 8,992,627 B2 | 3/2015 | Termanini |
| 10,722,381 B2 * | 7/2020 | Termanini ............. A61F 2/4609 |
| 2005/0131414 A1 | 6/2005 | Chana |
| 2007/0260256 A1 | 11/2007 | Beaule |
| 2008/0195111 A1 | 8/2008 | Anderson |
| 2011/0054628 A1 | 3/2011 | Banks et al. |
| 2012/0184964 A1 | 7/2012 | Hudak, Jr. et al. |
| 2013/0226183 A1 | 8/2013 | Xie |
| 2013/0345823 A1 | 12/2013 | Termanini |
| 2014/0156011 A1 | 6/2014 | Termanini |
| 2015/0010440 A1 | 1/2015 | Roudebush et al. |
| 2015/0313722 A1 | 11/2015 | Hudak, Jr. |

OTHER PUBLICATIONS

Written Opinion of the International Searching Authority for corresponding application PCT/US2016/047035 dated Oct. 28, 2016.
International Search Report for related application PCT/US2016/042445 dated Oct. 7, 2016.
Written Opinion of the International Searching Authority for related application PCT/US2016/042445 dated Oct. 7, 2016.

\* cited by examiner

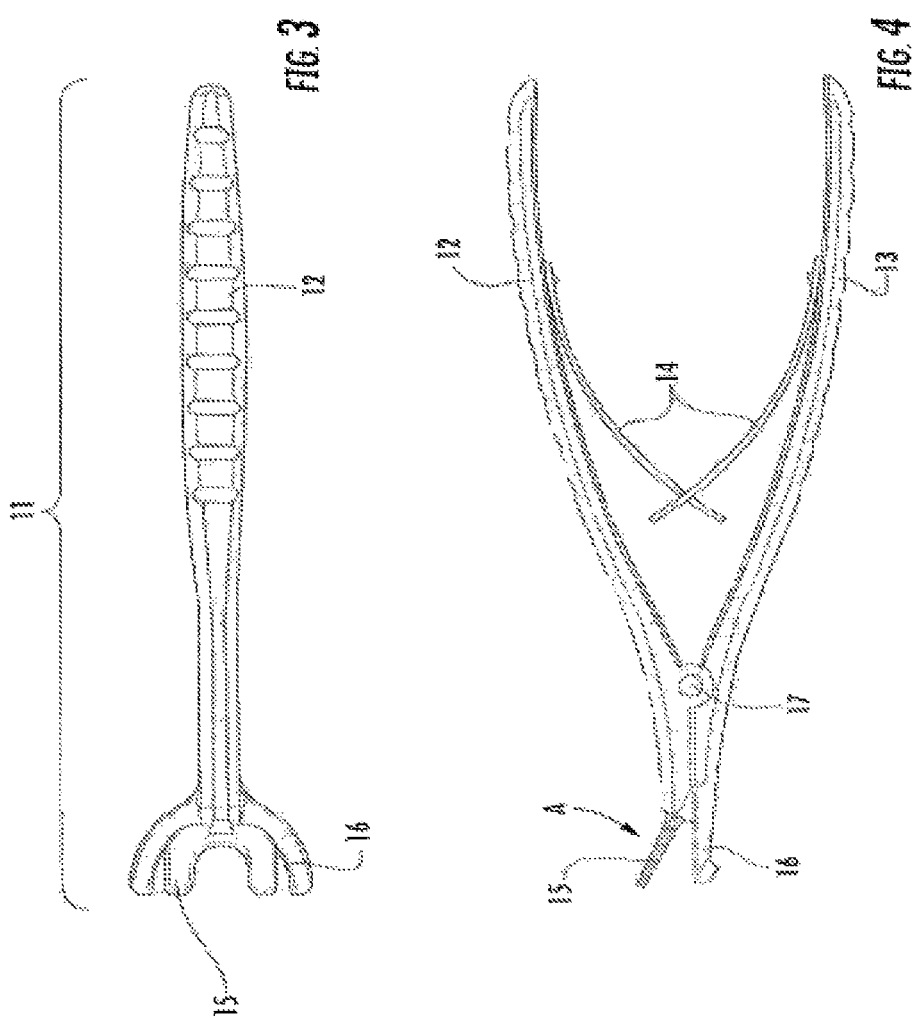

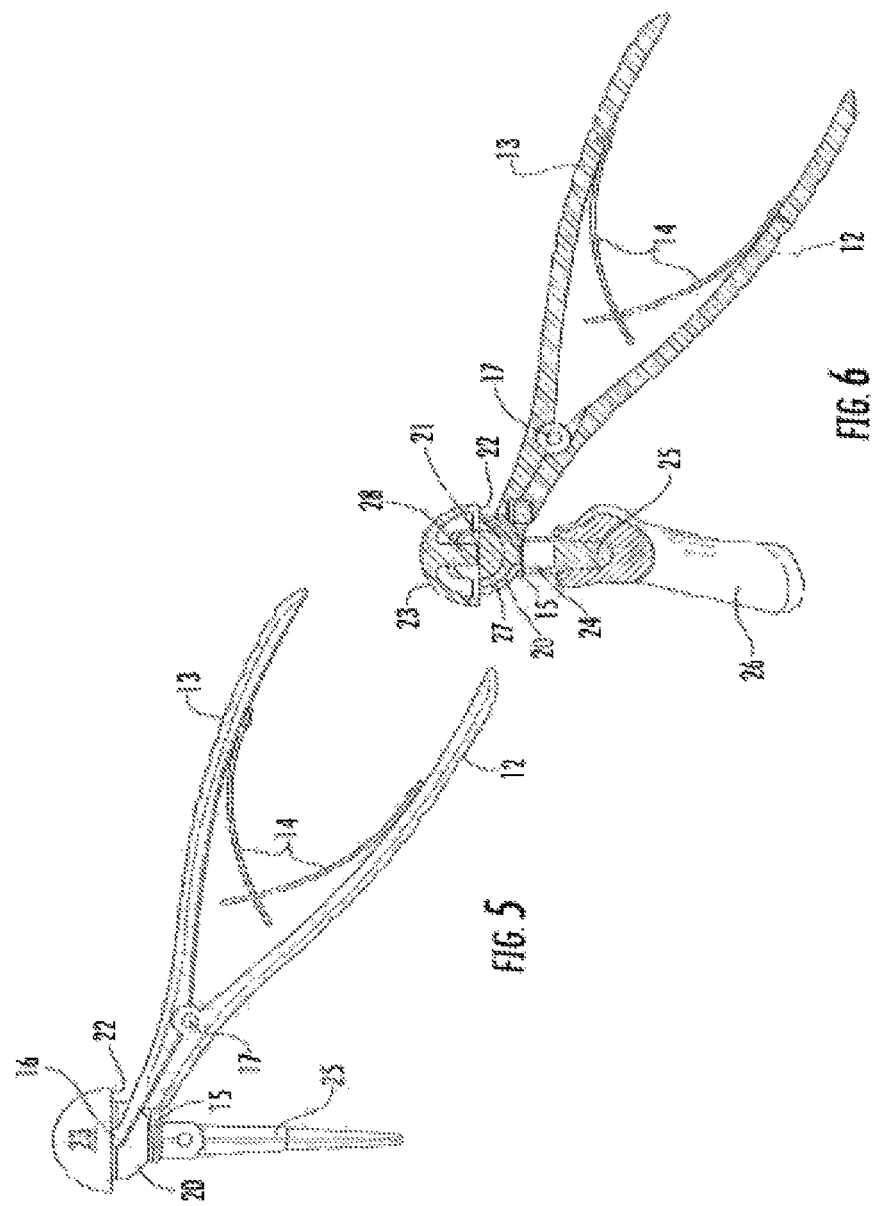

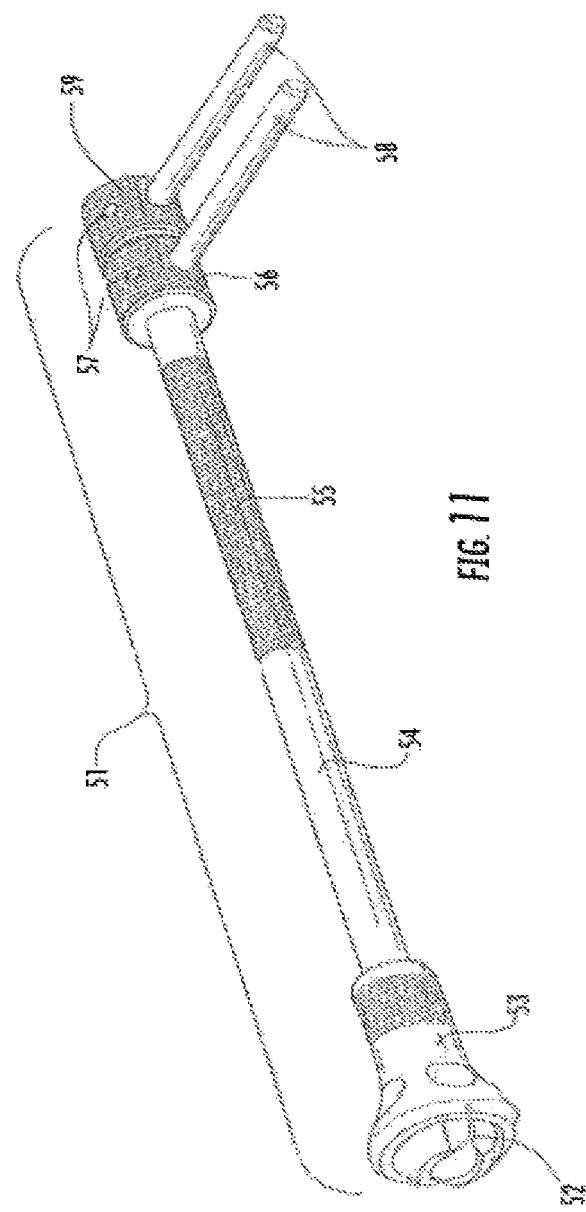

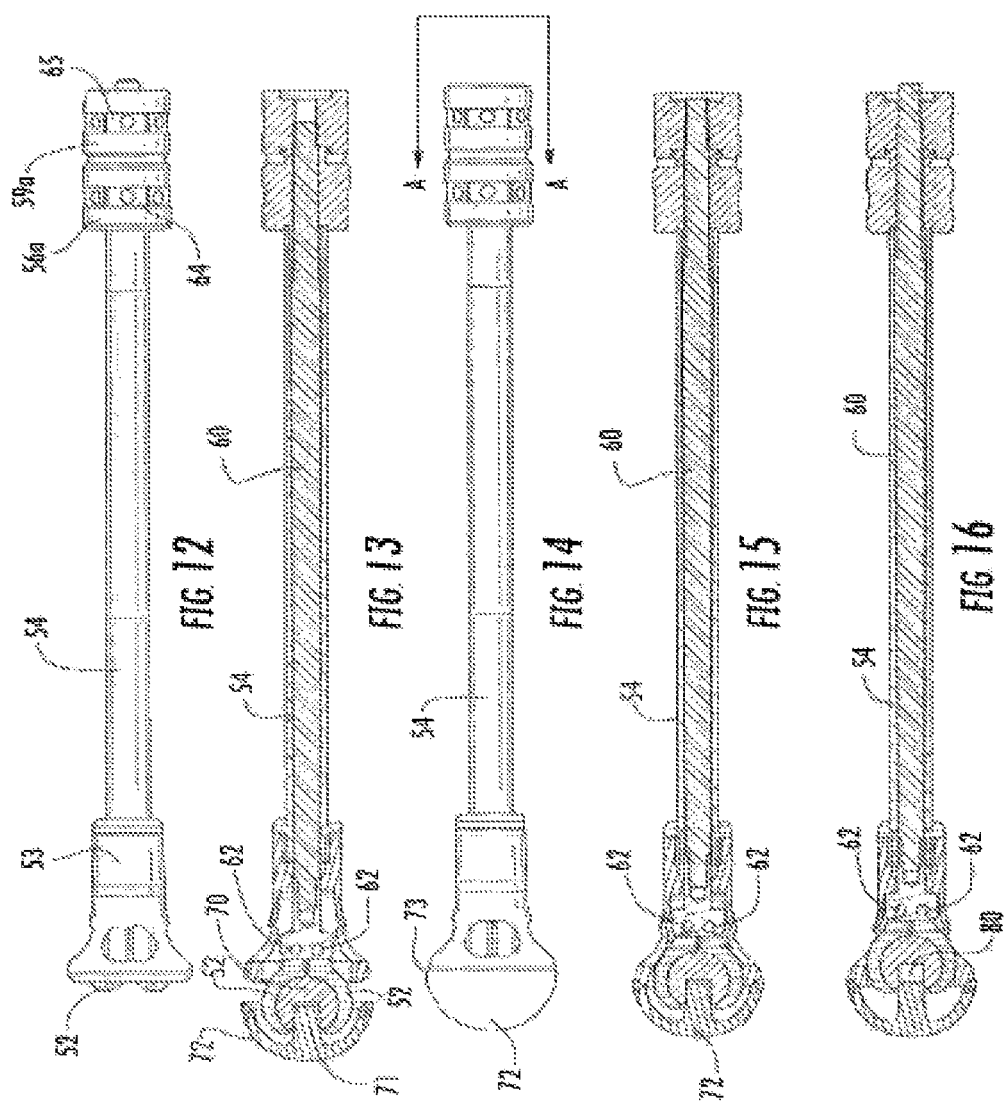

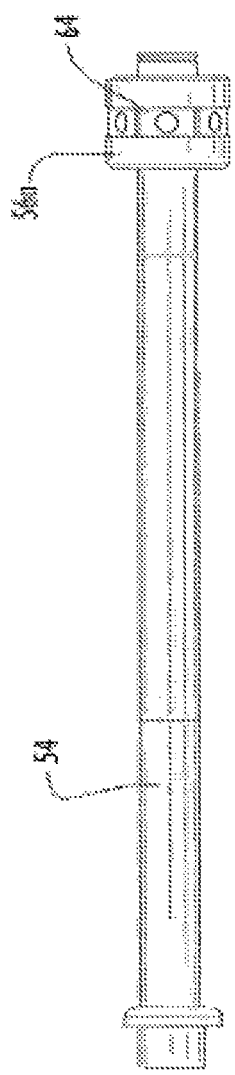
FIG. 17
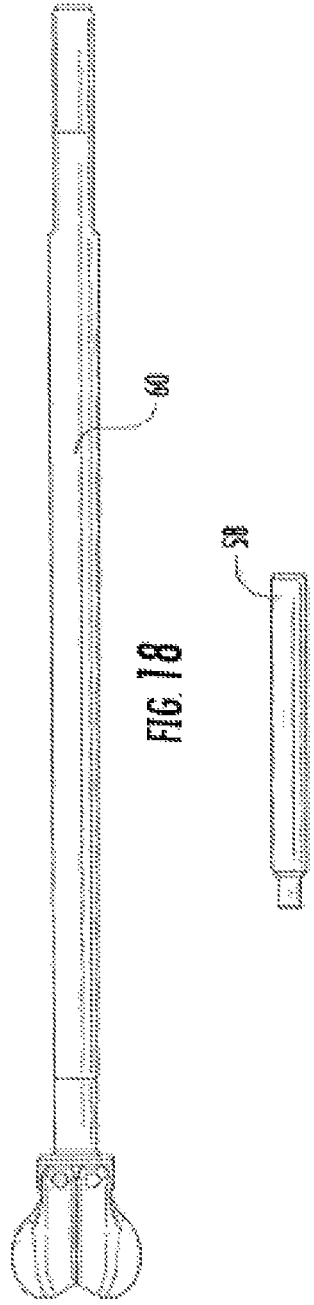
FIG. 18
FIG. 19
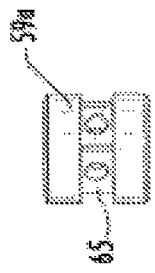
FIG. 21
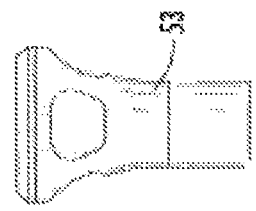
FIG. 20

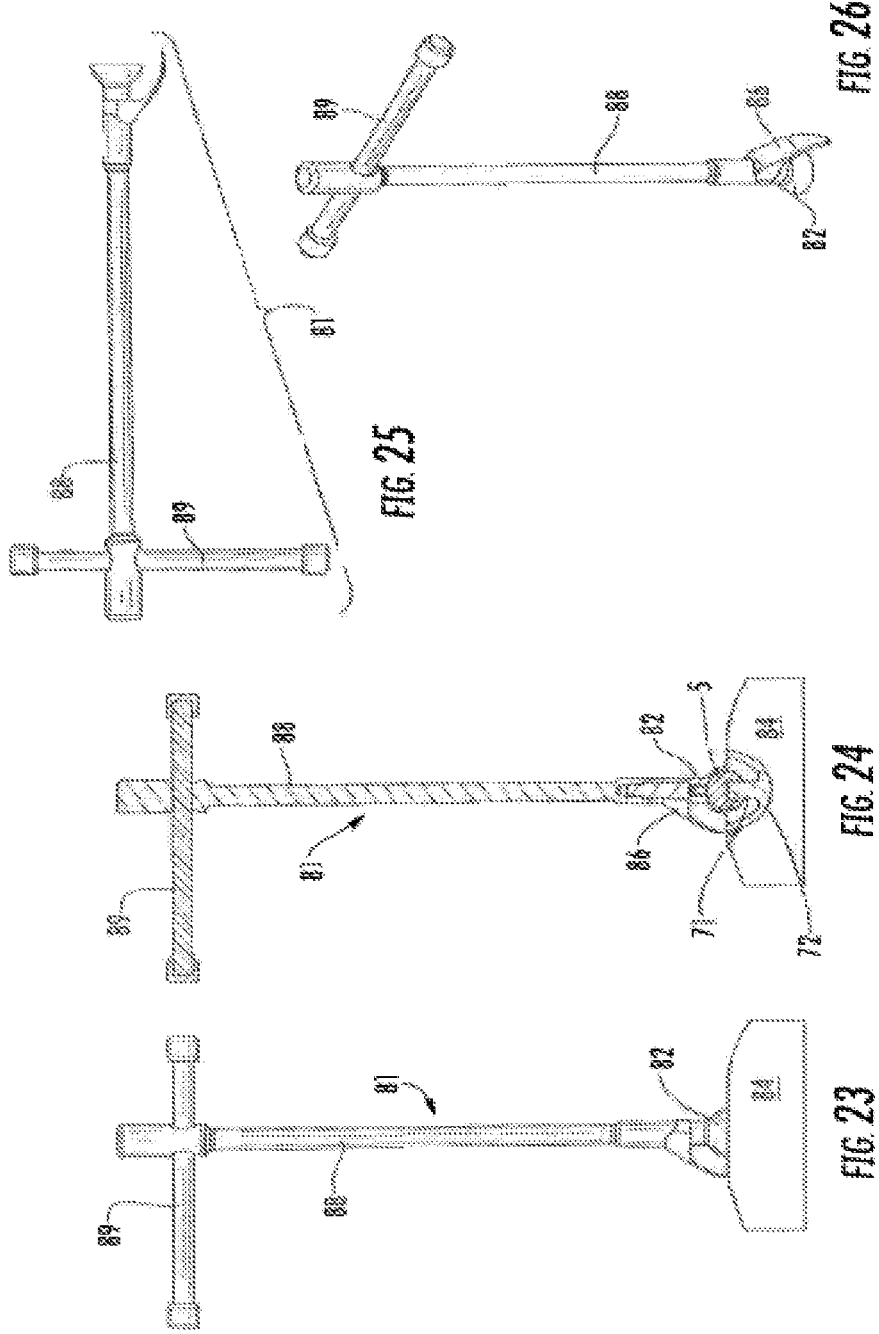

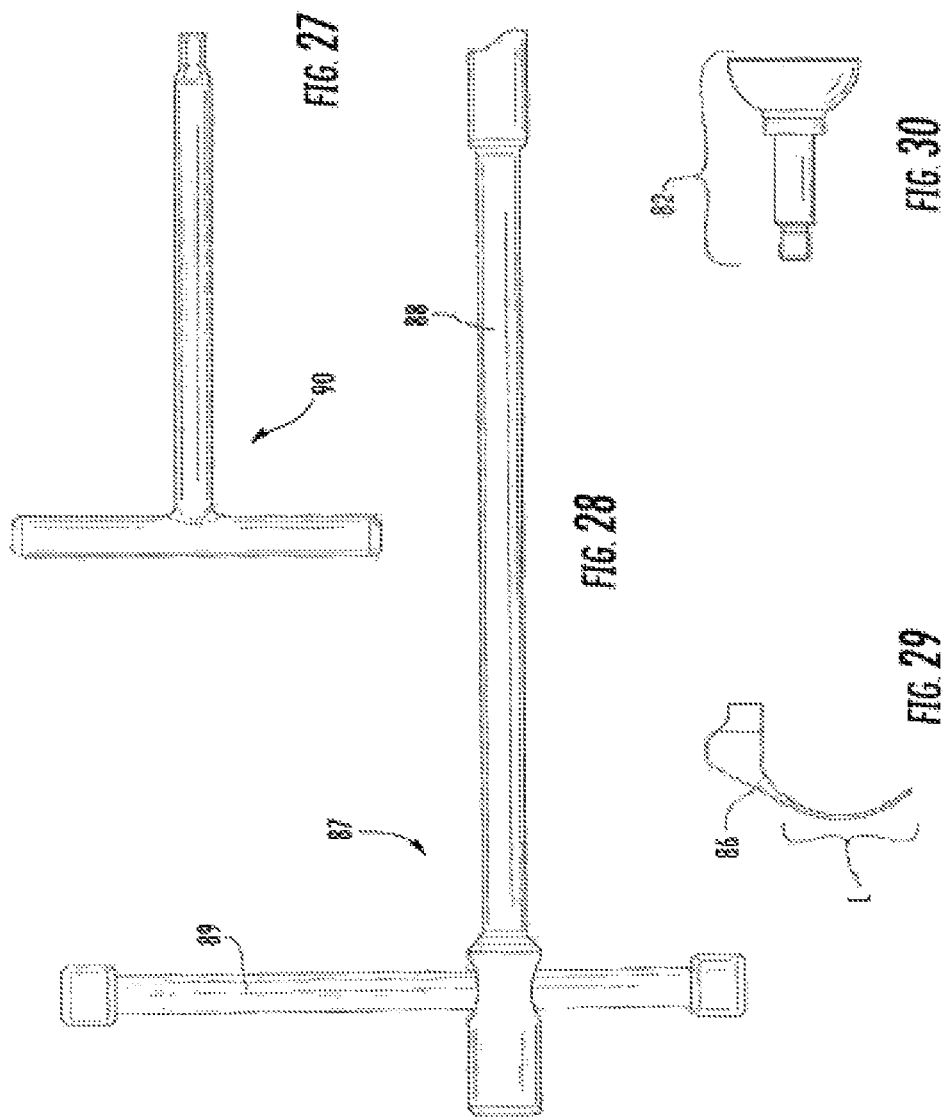

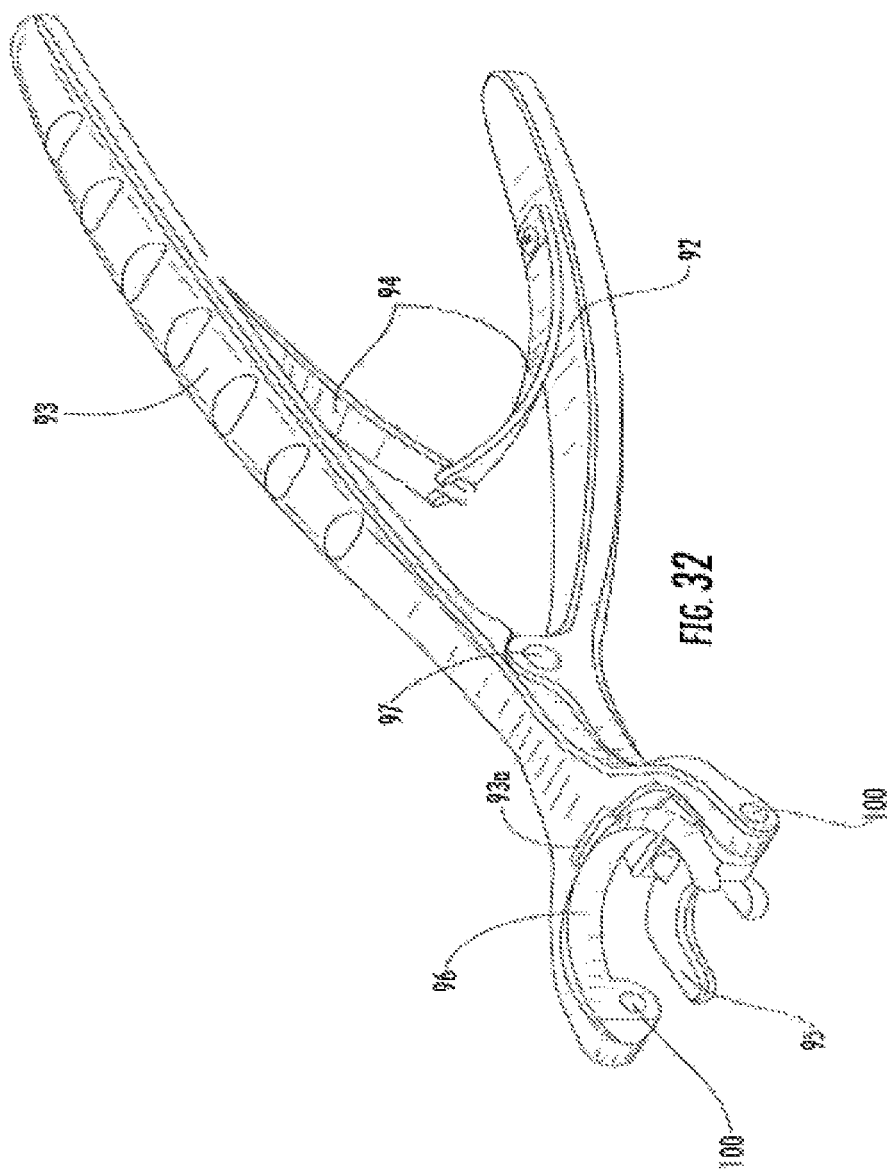

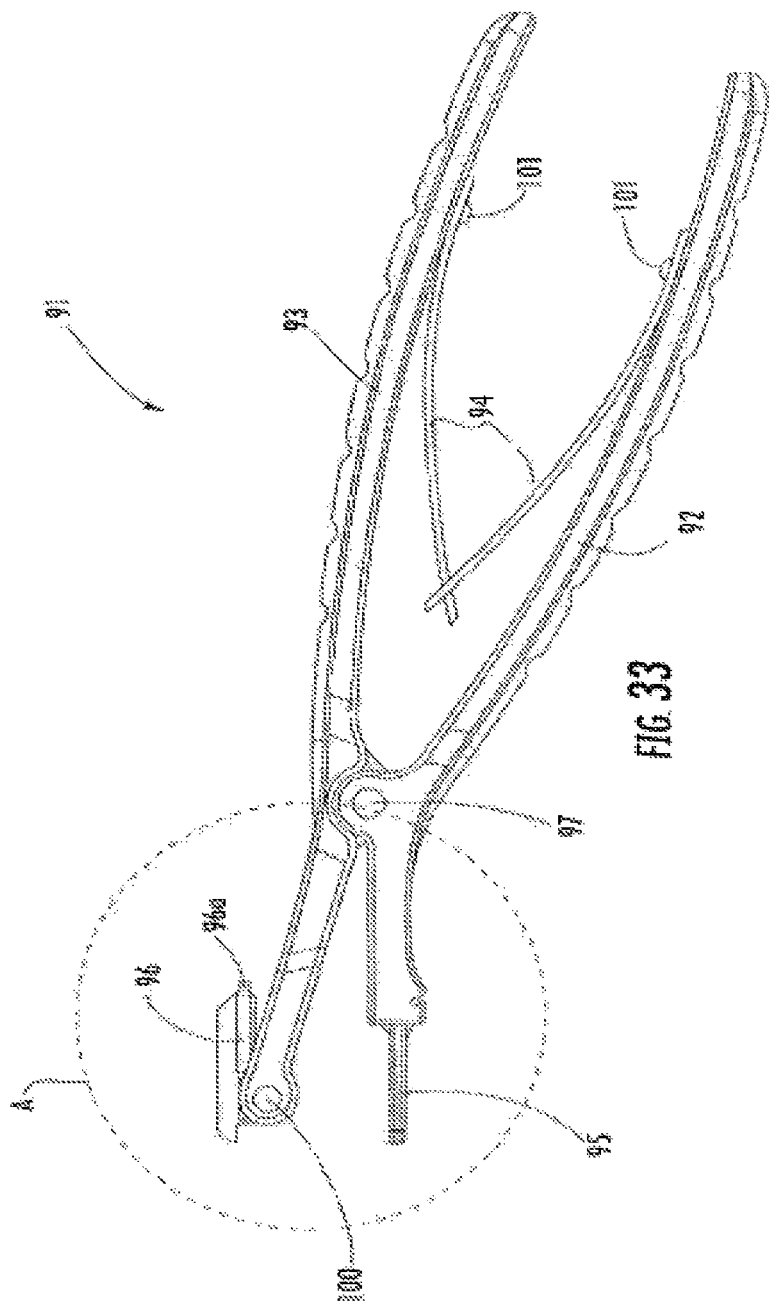

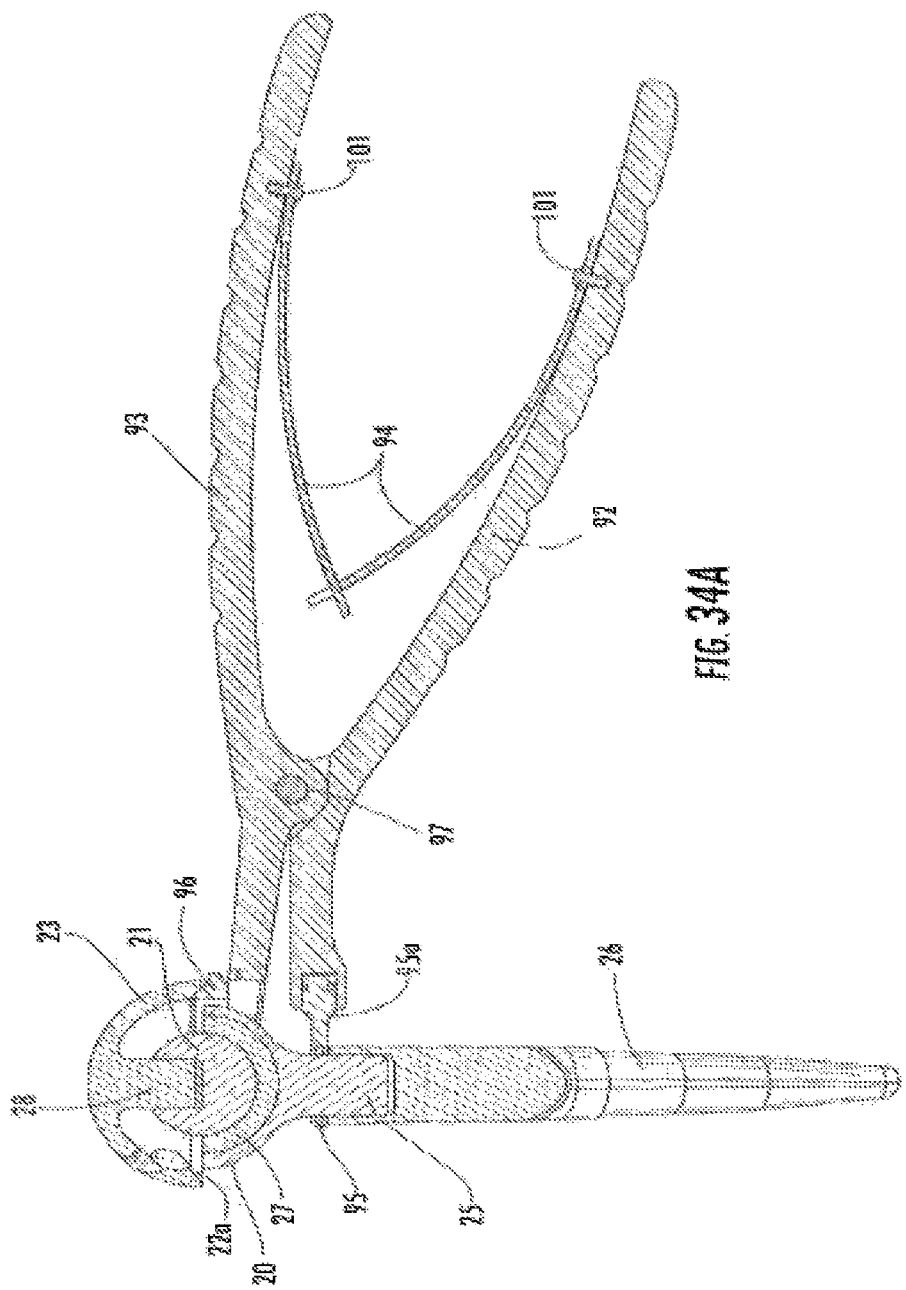

ized tools, and
SURGICAL TRAYS, INSTRUMENTS AND METHODS FOR REMOVING COMPONENTS OF A HIP REPLACEMENT PROSTHESIS This is an application filed as a continuation application of U.S. Ser. No. 15/749,380, now U.S. patent Ser. No. 10/722, 381, which in turn is based on U.S. Ser. No. 15/749,380, a 35 USC 371 application based on PCT/US2016/047035, which in turn is based on U.S. Ser. No. 62/210,652 filed 27.Aug.2015. The present application claims the full priority benefit of these prior applications and herein incorporates by reference the full disclosures of these prior applications.

BACKGROUND OF THE INVENTION

Field of the Invention

The present invention relates to surgical instruments and methods used in connection with removing components of a reverse hip prosthesis from a patient. More particularly, the invention has to do with instrument trays, surgical tools, and methods used in hip revision surgery.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, the reverse hip prosthesis generally comprises an acetabular ball affixed to a stem in an acetabular cup and a femoral cup affixed to a femoral implant or stem wherein the femoral cup articulates on the acetabular ball. The surgical trays, tools, and methods of the invention enable a surgeon to separate the femoral cup from the acetabular ball and remove components of the prosthesis from a patient in need of revision surgery. In the present disclosure we use the term "tools" from time to time to mean surgical tools.

BRIEF DESCRIPTION OF THE DRAWINGS

FIG. 3 is a top elevation view of a first embodiment of a cup and ball separator, i.e. a joint separator tool, of the invention.

FIG. 4 is a side elevation view of the first embodiment of the joint separator tool.

FIG. 5 is a side elevation view of the tool of FIG. 3 positioned on prosthesis just prior to separation of the femoral cup from the acetabular ball.

FIG. 6 is a section view of FIG. 5 with a partial section of a femur as an added element.

FIG. 11 is a perspective view of a first embodiment of an acetabular ball extractor of the invention.

FIG. 12 is an elevation view of a second embodiment of the acetabular ball extractor.

FIG. 13 is a section view of the acetabular ball extractor in a first step illustrating jaws of the acetabular ball extractor positioned over an acetabular ball which has been affixed in an acetabular cup.

FIG. 14 is an elevation view of the extractor of FIG. 13 in a second step fully engaged with the acetabular ball and cup.

FIG. 15 is a section view of FIG. 14 taken along section line A-A.

FIG. 16 is a section view of the extractor of FIG. 13 in a third step illustrating an acetabular ball separated from the stem of the acetabular cup.

FIG. 17 is an elevation view of a handle or outer shaft for the acetabular ball extractor.

FIG. 18 is an elevation view of a jaw assembly of the acetabular ball extractor.

FIG. 19 is a block bar lever of the acetabular ball extractor.

FIG. 20 is a handle bell of the acetabular ball extractor.

FIG. 21 is a shaft nut of the second embodiment of the acetabular ball extractor.

FIG. 23 is an elevation view of an acetabular cup extractor of the invention positioned on an implanted acetabular cup.

FIG. 24 is a section view of FIG. 23.

FIG. 25 is an elevation view of the acetabular cup extractor.

FIG. 26 is a perspective view of the acetabular cup extractor.

FIG. 27 is an elevation view of a driver used with the acetabular cup extractor.

FIG. 28 is an elevation view of a handle used with the acetabular cup extractor.

FIG. 29 is an elevation view of a blade used with the acetabular cup extractor.

FIG. 30 is an elevation view of an extractor cup used with the acetabular cup extractor.

FIG. 32 is a perspective view of a second embodiment of the joint separator tool wherein the handles have not been squeezed toward one another.

FIG. 33 is a side elevation view of the second embodiment of the joint separator tool of the invention wherein the handles have been squeezed toward one another.

FIG. 34A is a section view of FIG. 34.

DETAILED DESCRIPTION OF THE PREFERRED EMBODIMENTS

Figure 1:
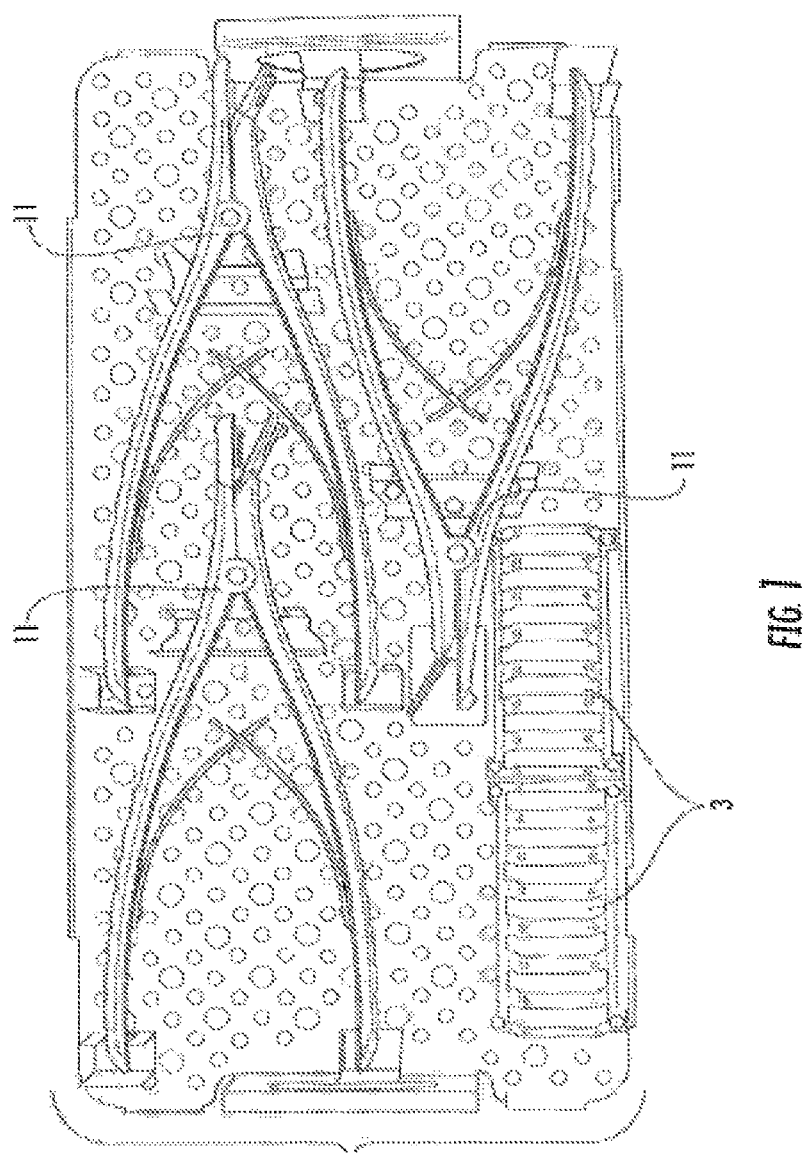
FIG. 1 illustrates the top portion of a tray containing tools for separating a femoral cup from an acetabular ball.
Figure 2:
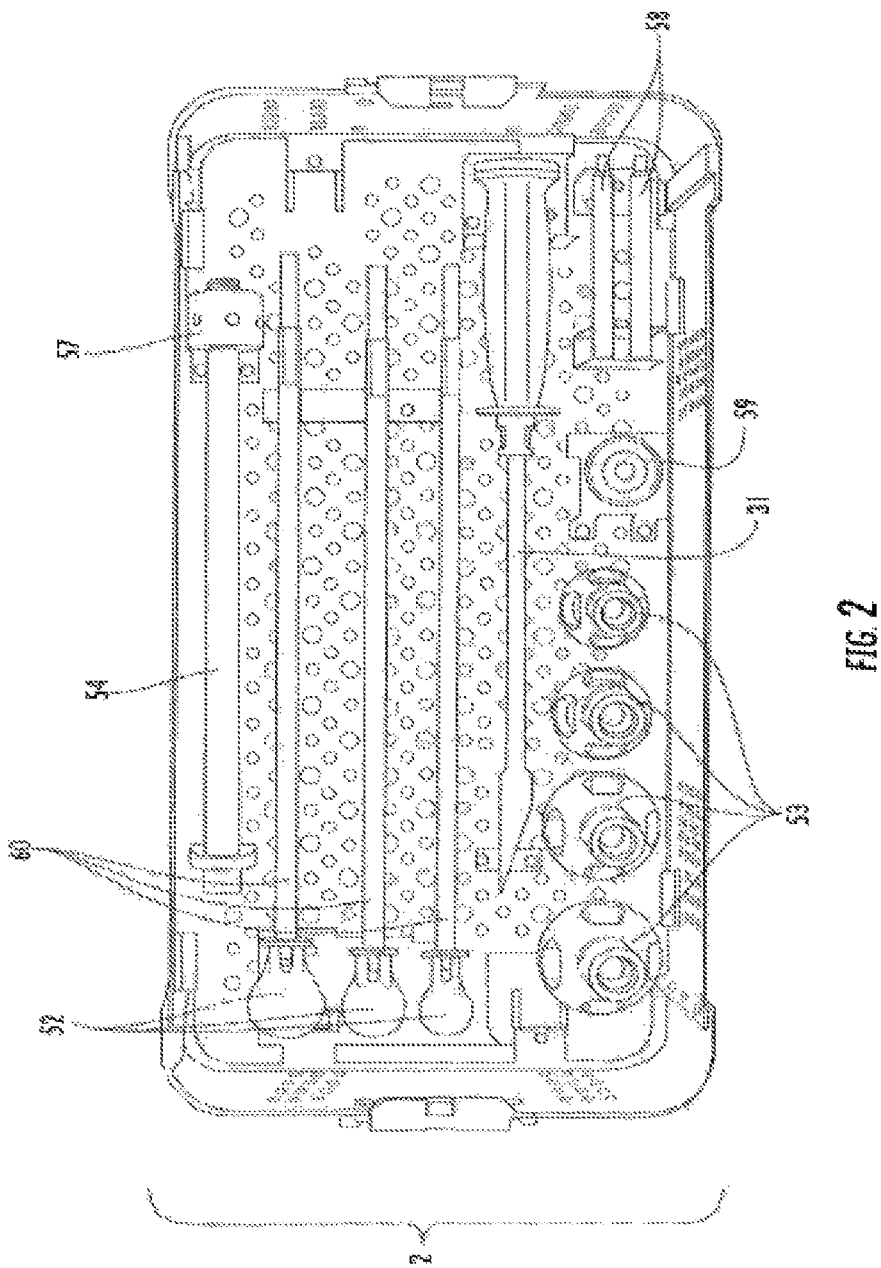
FIG. 2 illustrates the bottom portion of the tray of FIG. 1 containing tools for removing the femoral cup from the femoral implant and parts of a tool for removing the acetabular ball from the acetabular cup.

Referring to FIGS. 1 and 2, the surgical tray of the invention is comprised of a top portion 1 and a bottom portion 2. The top portion 1 contains spacers 3 and three sizes, small, medium and large, of the first embodiment of the joint separator tools 11 which are illustrated in detail in FIGS. 3 and 4. Of course, the second embodiment 91 of the joint separators can be included in this tray instead of the first embodiment. FIGS. 32-34 illustrate the second embodiment in detail. The different sizes are adapted to separate paired cups and balls of different sizes as used in implants having different sizes.

The elements of joint separator tools 11 illustrated in FIGS. 3 and 4 include a first handle 12 and a second handle 13. Springs 14 tend to bias the handles apart from one another as illustrated in FIG. 4. The distal end of the first handle 12 has a femoral engagement component 15 and a distal end of the second handle 13 has an acetabular engagement component 16. Pivot pin 17 hinges the first handle 12 to the second handle 13 so that when the handles are squeezed toward one another the femoral engagement component 15 and the acetabular engagement component 16 are moved away from one another, thereby separating the femoral cup from the acetabular ball. The hinge allows the surgeon to push the femoral cup aside while maintaining pressure on the handles so that the cup does not return to the ball.

Figure 3A:
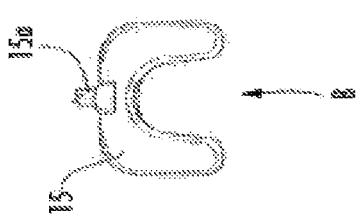
FIG. 3A is a top elevation view of a femoral engagement component of the first embodiment of joint separator tool.
Figure 3B:
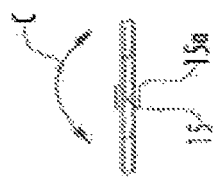
FIG. 3B is an end elevation view of FIG. 3A with arrow C showing the directions in which the component can move.

The femoral engagement component 15 illustrated in FIG. 3A is viewed from the direction of arrow A in FIG. 4. Femoral engagement component 15 is rotatably connected to first handle 12 by means of pivot pin 15a (partially illustrated). In FIG. 3B, an end view of femoral engagement component 15 is illustrated as taken from the direction of arrow B in FIG. 3A. Arrow C in FIG. 3B illustrates the directions in which femoral engagement component 15 can be rotated.

Figure 4A:
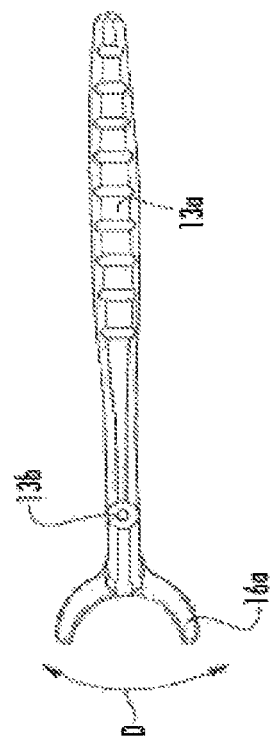
FIG. 4A is a bottom elevation view of an alternate first embodiment of the joint separator tool.
Figure 4B:
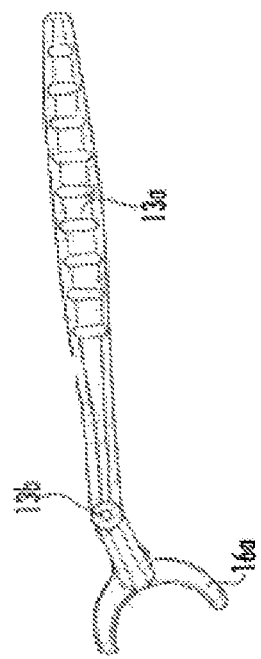
FIG. 4B is the same view as FIG. 4A following movement of an acetabular engagement component of the joint separator tool.

FIGS. 4 and 4B illustrate a bottom elevation view of an alternate embodiment of the second handle which is designated as 13a. A hinge 13b is provided on handle 13a to allow pivoting of a portion of the handle located between pivot pin 17 (see FIG. 4) and acetabular engagement component 16a. Pivoting is allowed in the directions of arrow D of FIG. 4A. FIG. 4B provides an example of a pivoted handle 13a having a component 16a at the distal end thereof.

In FIGS. 5 and 6, the joint separator 11 is positioned on a prosthesis just prior to separation of the femoral cup 20 from the acetabular ball 21. The acetabular engagement component 16 is engaged with the circumferential edge 22 of acetabular cup 23 and the femoral engagement component 15 is engaged with the neck 24 of femoral cup 20. A femoral implant 25 is also illustrated in FIG. 6 and femur 26 is shown in partial section. A liner 27 is illustrated in femoral cup 20. The acetabular ball 21 is affixed to stem 28 of the acetabular cup.

When handles 12 and 13 or 12 and 13a are squeezed toward one another and the separator is positioned as illustrated in FIGS. 5 and 6, the femoral cup is separated from the acetabular ball.

The second embodiment of the joint separator of the invention is very similar to the first embodiment except for the acetabular engagement element. This embodiment is illustrated in FIGS. 32-34A and it is designated as tool 91. A pivotable partial ring, referred to herein as acetabular engagement ring 96, is employed to engage the acetabular cup in the second embodiment as distinguished from acetabular engagement component 16 in the first embodiment. The term "acetabular engagement element" may be used herein to refer to both the acetabular engagement component 16 and the acetabular engagement ring 96.

Figure 33A:
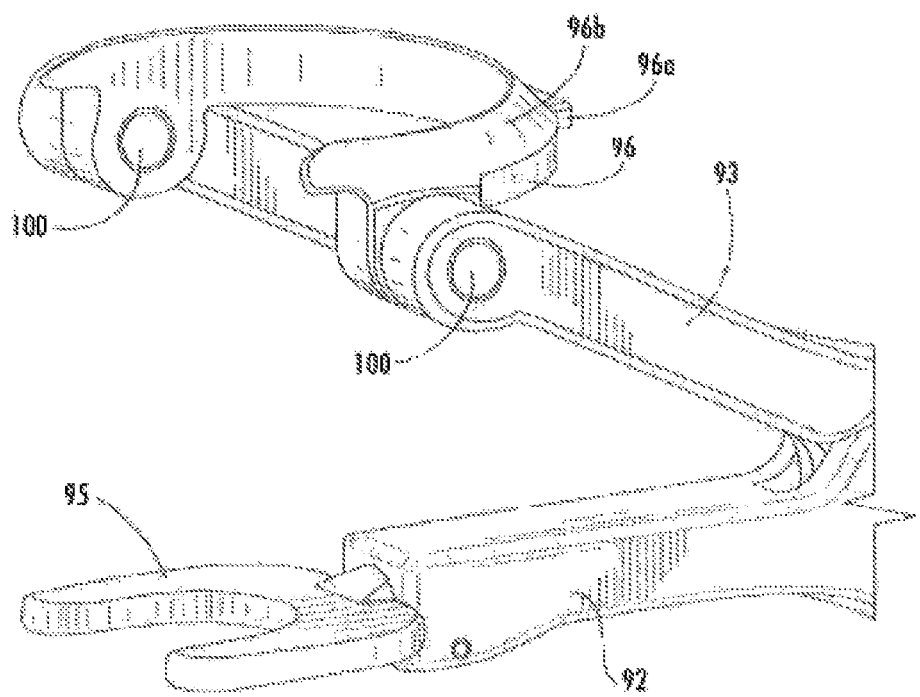
FIG. 33A is a perspective view of portion A of FIG. 33.
Figure 34:
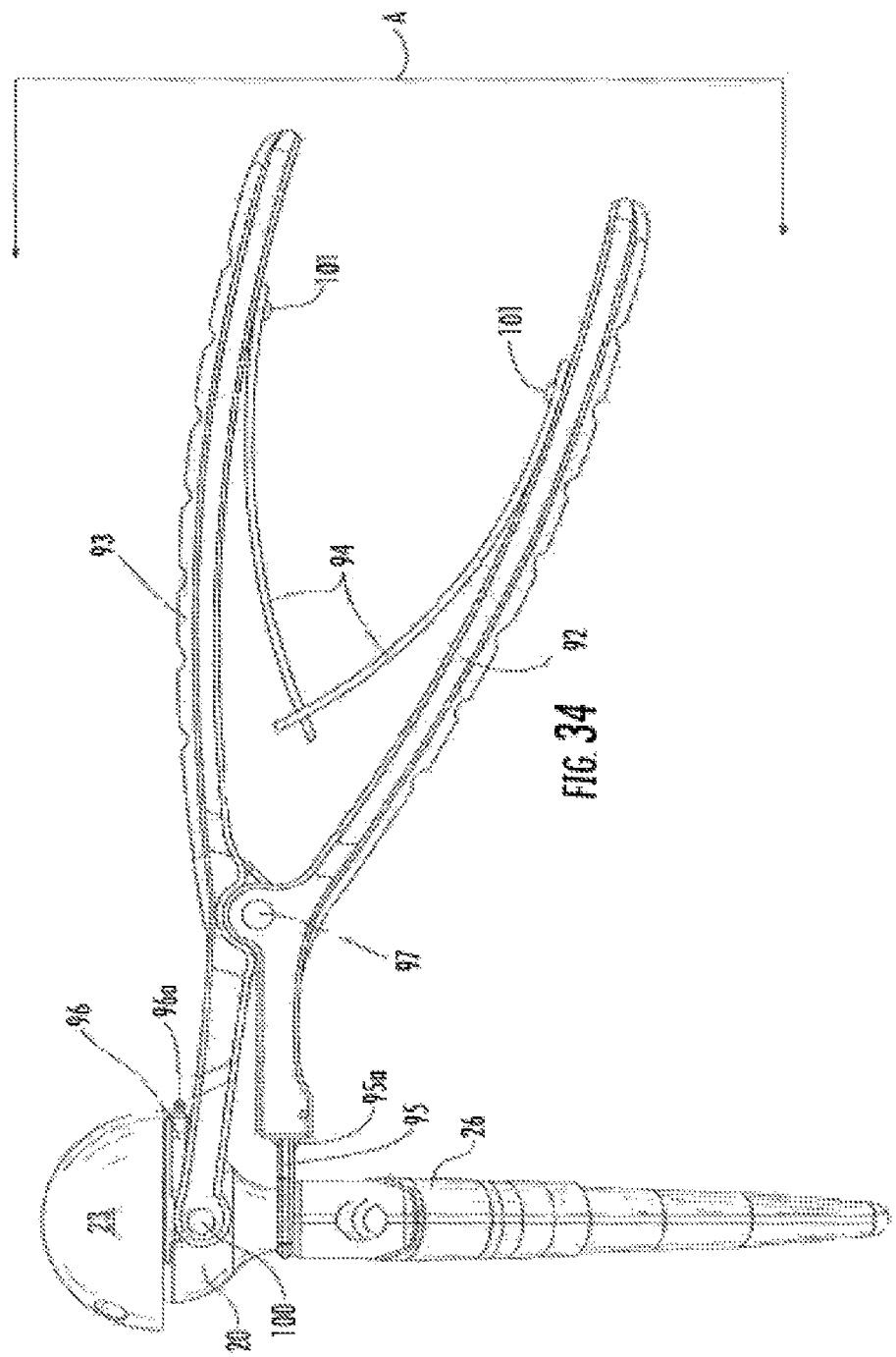
FIG. 34 is a side elevation view of the second embodiment of the joint separator tool engaged with a femoral implant/cup and an acetabular cup before the femoral cup and acetabular cup are separated from one another.

FIG. 33 is a side elevation view of joint separator tool 91. The tool has a first handle 92 and a second handle 93. Springs 94, affixed to the handles with screws 101, tend to bias the handles apart from one another. And in FIG. 33, the handles have been squeezed toward one another to an intermediate position between fully open as shown in FIG. 32 and closed. The distal end of first handle 92 has a femoral engagement component 95 attached thereto. The distal end of second handle 93 has an acetabular engagement ring 96 pivotably attached thereto by means of ring pins 100. (See also FIG. 33A.) As can be seen from the drawings, ring 96 is pivotable about an axis which is perpendicular to the central axis of the distal portion of handle 93. Fulcrum pin 97 hinges the first handle 92 to the second handle 93 so that when the handles are squeezed toward one another the femoral engagement component 95 and the acetabular engagement ring 96 are moved away from one another. The pin 97 thus provides a fulcrum between the first and second handles.

As in the first embodiment of the joint separator 11, the femoral engagement component 95 of the second embodiment may be rotatably connected to first handle 92 by means of axis pin 95a. Axis pin 95a allows the femoral engagement component 95 to rotate axially about the central axis of the first handle 92 in the same manner as femoral engagement component 15 is allowed to rotate axially about the central axis of first handle 12 in the first embodiment. The alternate embodiment of second handle 13a which has a hinge 13b as described above (see FIG. 2B) can also be used with the second embodiment of the joint separator of the invention.

Referring to FIGS. 33A and 34A, acetabular engagement ring 96 has a beveled edge 96b which engages a beveled edge 22a of acetabular cup 23. Ring 96 also has a tab 96a which is seated in an indent 93a to prevent downward rotation of ring 96 below the horizontal central plane of the distal end of handle 93. Thus, as can be seen in FIG. 32 wherein the handles are in the fully open position, tab 96a is seated in indent 93a and ring 96 is prevented from downward rotation in that position.

In FIGS. 34 and 34A the tool 91 is positioned on a prosthesis just prior to separation of the femoral cup 20 from the acetabular ball 21. The beveled edge 96b of acetabular engagement ring 96 is engaged with a circumferential beveled edge 22a of acetabular cup 23 and the femoral engagement component 95 is engaged with the neck 25 of femoral cup 20 or the outer hemispherical surface of femoral cup 20, or both the neck 25 and the outer hemispherical surface of femoral cup 20. A femoral implant 26 is also illustrated and the femoral engagement component 95 may also engage the top (i.e., the proximal end) of implant 26. A liner 27 is illustrated in femoral cup 20. The acetabular ball 21 is affixed to stem 28 of acetabular cup.

When handles 92 and 93 are squeezed toward one another the femoral cup is separated from the acetabular ball.

The components in tray bottom portion 2 of FIG. 2 include a femoral cup extractor 31 and elements of an acetabular ball extractor 51. (See also FIGS. 7-22A.) A femoral cup extractor of the type described in our U.S. provisional application Ser. No. 62/369,901, filed on Aug. 2, 2016, can be used in place of extractor 31. The provisional application is incorporated by reference herein in its entirety.

Figure 7:
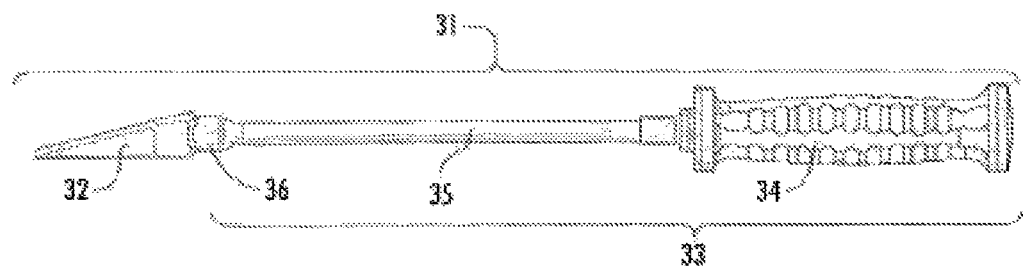
FIG. 7 is an elevation view of a femoral cup extractor of the invention.

The femoral cup extractor 31 of FIG. 7 has a forked wedge 32 affixed to the distal end of a driver 33. The driver 33 is comprised of a handle 34 at its proximal end and a shaft 35 with a connector 36 at its distal end. The proximal end of the shaft 35 is affixed to the distal end of handle 34.

Figure 8:
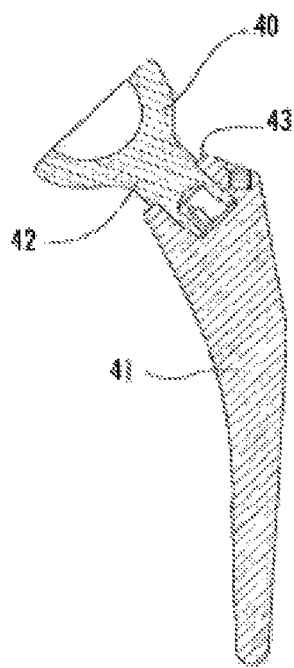
FIG. 8 is a section view of a femoral cup secured to a femoral implant by means of a Morse taper.

A femoral cup 40 affixed by a Morse taper to a femoral implant 41 is illustrated in section in FIG. 8. The femoral cup 40 has a neck 42 and the proximal end of the femoral implant is designated by the reference numeral 43.

When the femoral implant, with a femoral cup affixed therein, is implanted in the proximal end of a femur, it may be desirable to remove the femoral cup without disturbing the femoral implant. In this way, the femoral implant can be maintained in the femur without disturbing bone ingrowth. Thus, it is desirable to "break" the secure Morse taper connection between the femoral cup and the femoral implant without pulling on the implant. This is achieved by using the surgical tool of the present invention.

Figure 9:
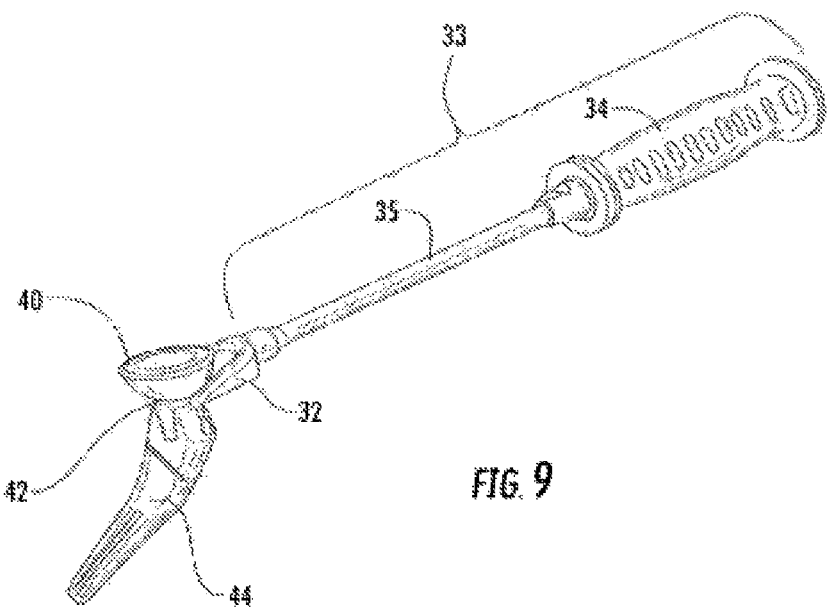
FIG. 9 is perspective view of the femoral cup extractor positioned on the femoral cup just prior to extraction of the femoral cup from the femoral implant.
Figure 10:
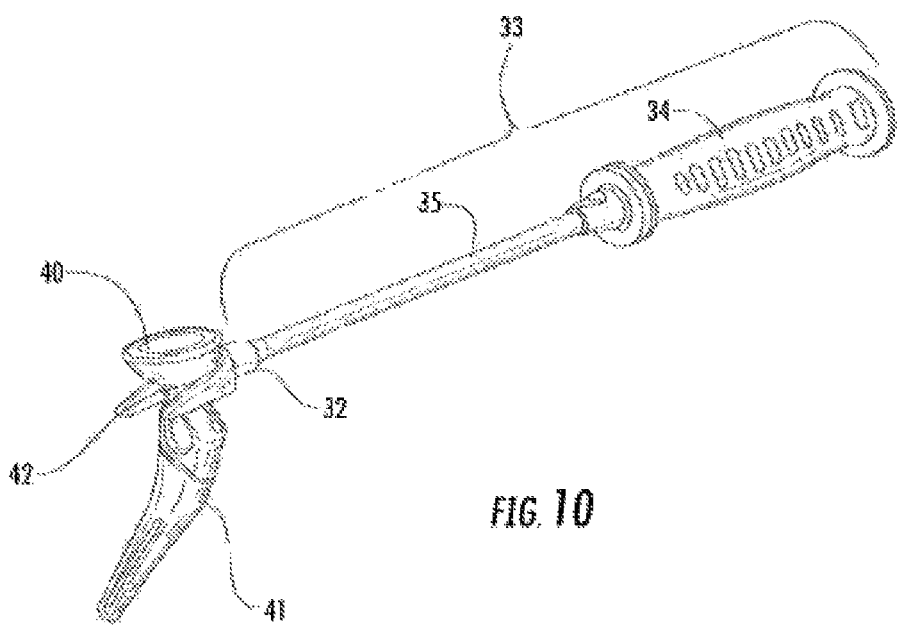
FIG. 10 is a perspective view of the femoral cup extractor positioned relative to the femoral cup and the femoral implant following impacting to loosen the cup from the Morse taper.

According to the method of the invention, the wedge 32 of the femoral cup extractor 31 is positioned relative to the femoral cup 40 and the femoral implant 41 as illustrated in FIG. 9. Then the proximal end of handle 34 is struck with a hammer to drive wedge 32 toward femoral cup 40 with sufficient force to lift the cup upwardly while keeping the femoral implant securely embedded in the femur. Thus, the cup is no longer affixed to the femoral implant 41 by means of the Morse taper. This position is illustrated in FIG. 10. The cup can then be picked up and removed by hand.

The femoral cup extractor 31 can also be used with a conventional hip implant where a femoral ball is affixed to a femoral implant by means of a Morse taper.

Figure 22:
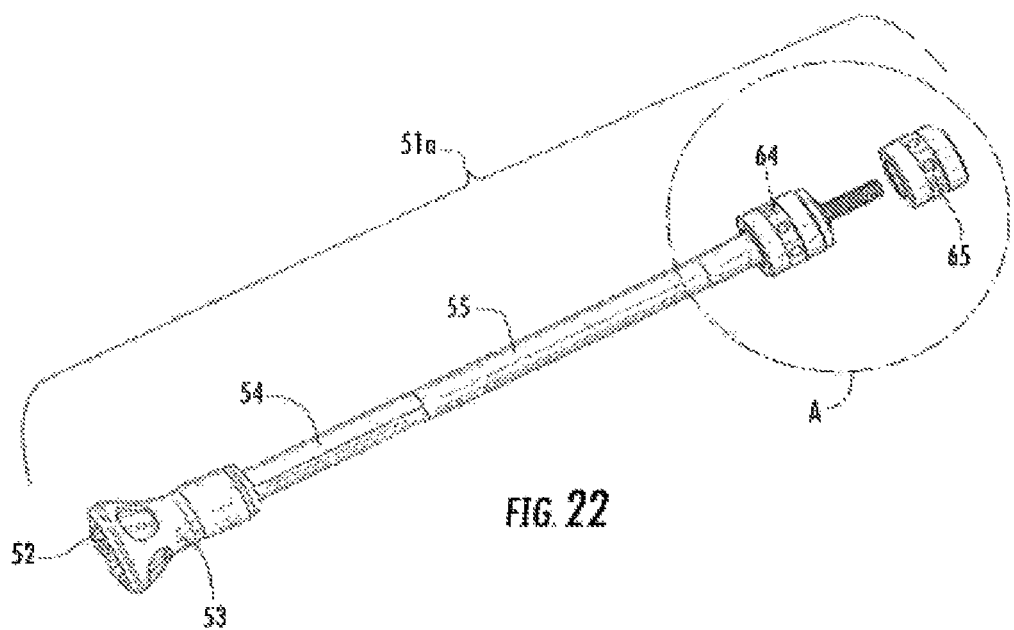
FIG. 22 is a partially exploded view of the second embodiment of the acetabular ball extractor.
Figure 22A:
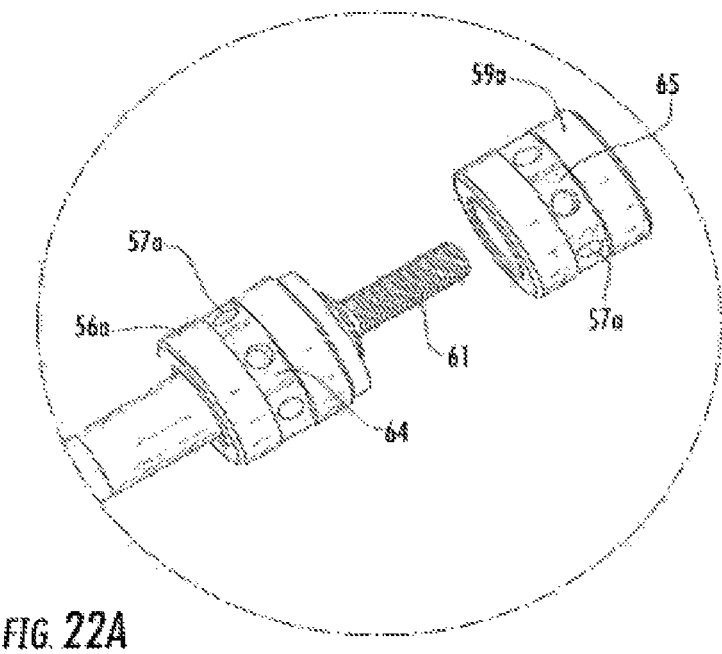
FIG. 22A is a magnified view of the proximal end of the embodiment of FIG. 22.

A first embodiment of the acetabular ball extractor 51 of the invention is illustrated in perspective in FIG. 11. The tool 51a is the second embodiment of the acetabular ball extractor of the invention and it is illustrated in elevation in FIG. 12 and in a partially exploded view in FIG. 22. The tool comprises jaws 52 and handle bell 53 at its distal end. The jaws element of tool 51 or 51a is provided in two or more than two different sizes and the handle bell element of the tool 51 or 51a is provided in two or more than two different sizes, each being adapted to work in coordination to remove an acetabular ball of a particular size or range of sizes. Outer shaft 54 has an optionally knurled portion 55 along the length hereof. At the proximal end of tool 51, a shaft nut 56 is affixed to shaft 54 and at the proximal end of tool 51a, a shaft nut 56a is affixed to shaft 54. The surface of shaft nut 56 is optionally knurled and holes 57 are disposed radially thereon to receive block bar 58 for leverage when operating the tool. Jaw shaft nut 59 or 59a is threaded onto the jaw shaft 60. Jaw shaft 60 is illustrated in section in FIGS. 13, 15 and 16, and in elevation in FIG. 18. FIGS. 22 and 22A illustrate the threaded proximal end 61 of jaw shaft 60.

The difference between tools 51 and 51a has to do with differences in shaft nuts 56 and 56a and jaw shaft nuts 59 and 59a. Shaft nuts 56 and 59 are knurled and holes 57 are provided in the knurled portions to receive block bars 58 which are used to provide leverage in the operation of the tool. Shaft nuts 56 and 59a are also knurled but they are provided with hex portions 64 and 65, respectively. Holes 57a are provided for block bars 58 in hex portions 64 and 65. The hex portions allow the surgeon to use a wrench or wrenches instead of some or all of the block bars in order to obtain increased leverage during the operation of the tool.

The operation of the tool is illustrated in FIGS. 13-16. The jaws 52 are allowed to open when jaw shaft 60 is pushed into a distal direction while holding shaft 54 so that the jaws move out of handle bell 53. The jaws 52 are hinged by pins 62. In FIG. 13 the jaws 52 are shown in section after they have been pushed out of handle bell 53 and pushed over acetabular ball 70. Acetabular ball 70 is securely affixed by means of a Morse taper on stem 71. Stem 71 is affixed to and projects from the concave surface off acetabular cup 72.

In FIGS. 14 and 15 the distal end of handle bell 53 has been pushed into engagement with the circumferential edge 73 of acetabular cup 72. When the tool has been engaged with the ball and cup in this manner, the next step is to grip shaft 54 while turning shaft nut 59 or 59a causing the jaw shaft to move in a proximal direction so that jaws 52 pull on acetabular ball 70 while handle bell 53 exerts an opposing force on the circumferential edge 73 of acetabular cup 72. The opposing force prevents pulling on acetabular cup 72 so that the cup is not pulled out of the acetabulum. A block bar lever 58 is placed in a hole 57 or 57a of shaft nut 56 or 56a and another block bar lever 58 is placed in a hole 57 or 57a of jaw shaft nut 59 or 59a when additional leverage is needed to exert a pulling force on acetabular ball 70 and an opposing pushing force on acetabular cup 72. If more leverage is needed, the block bar levers 58 are removed from one or both of shaft nuts 56a or 59a and a wrench Is used on either or both shaft nuts by placing the open end of the wrench(es) (not shown) over one or both hex portions 64 or 65. When sufficient force is exerted, the ball separates from stem 71 as illustrated by space 80 in FIG. 16.

Generally speaking, in the surgical method of using the tools from the surgical trays, the first step is to separate the femoral cup from the acetabular ball and then, in any order, the femoral cup is removed from the femoral implant and the acetabular ball is removed from the acetabular cup. More specifically, before separating the femoral cup from the acetabular ball, the appropriately sized joint separator tool is selected. The size is selected based upon the size of the implanted acetabular ball and femoral cup. Similarly, before removing the acetabular ball from the acetabular cup the appropriately sized jaw and bell elements of the acetabular ball extractor are selected on the basis of the size of the implanted acetabular ball.

An acetabular cup extractor 81 is positioned in FIGS. 23 and 24 on an acetabular ball 5 which is affixed to the stem 71 of acetabular cup 72. The acetabular cup 72 is implanted in a bone 84, the bone being an acetabulum. The extractor cup 82 is in articulating contact with acetabular ball 5 and the distal end of blade 86 is positioned between cup 72 and bone 84. In a surgical method of the invention, the extractor cup 82 is carefully rotated on acetabular ball 5 to cause blade 86 to move along or in close proximity to the convex surface of acetabular cup 72. Blade 86 comes in various sizes such that the portion of the blade designated as "L" in FIG. 28 varies in length. Multiple blades of different lengths can be used, always starting with the shortest blade length, then using the next longest length, etc. For example, if three blades are used, the shortest length blade is used first and at least one complete rotation of the blade between the acetabular cup 72 and the bone 84 is completed. In other words, the blade 86 is rotated at least 360 degrees around the cup. Then the next longest blade length is used and at least one complete rotation of the blade between the acetabular cup 72 and bone 84 is completed. This process is repeated with the next longest blade, i.e. the longest of the three blades, thereby loosening the connection between the acetabular cup 72 and bone 84 so that the acetabular cup 72 is sufficiently loosened that it can be lifted out of bone 84. Since blade 86 moves along or in close proximity to the convex surface of acetabular cup 72, bone damage is minimized even if there has been significant bone ingrowth prior to the removal process. The process is conducted carefully in order to minimize the risk of damage to the bone.

Figure 31:
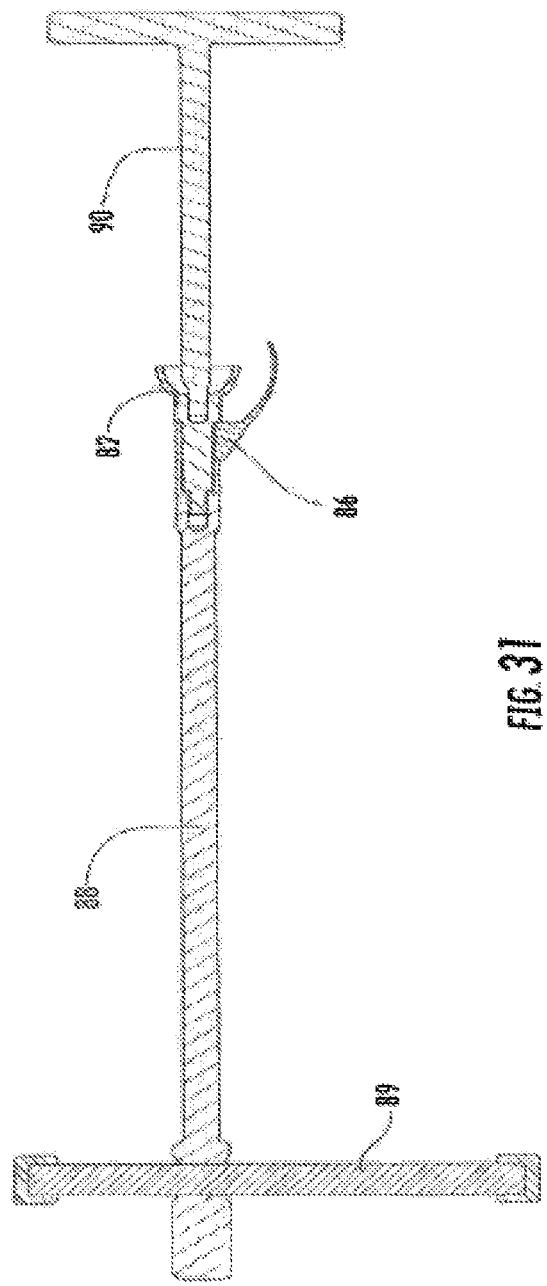
FIG. 31 is a section view of the acetabular cup extractor of FIG. 25 and the driver of FIG. 27.

In addition to the extractor cup 82 and blade 86, the acetabular cup extractor 81 is comprised of a handle 87 made of a shaft 88 and a movable lever arm 89. Driver 90, illustrated in elevation in FIG. 27, is used to fasten and unfasten the extractor cup 82 to and from shaft 88 of handle 87. A section view illustrating the position of these elements in the fastening and unfastening operations is provided in FIG. 31.

In the surgical method of removing the acetabular cup, any screws or other connectors extending from acetabular cup 72 into bone 84 are removed. Then blade 86 is pushed into the bone adjacent the convex surface of the acetabular cup until the extractor cup 82 is in contact with acetabular ball 5. Then, while pressing the extractor cup 82 against the acetabular ball 5, the acetabular cup extractor 81 is rotated on acetabular ball 5, thereby causing blade 86 to loosen the connection between acetabular cup 72 and the bone 84. When the acetabular cup 72 is sufficiently loosened from bone 84 after using blades 86 of increasing length as explained above, the acetabular cup is lifted out of the bone.

The invention claimed is:

1. Surgical tray apparatus and components thereof comprising:
   a set of trays comprising tools for use in hip revision surgery which operate to separate
   i) a femoral cup from an acetabular ball, or
   ii) a femoral cup from a femoral implant, or
   iii) an acetabular ball from an acetabular cup;
   having:
   A) as tool configured for use in separating a femoral cup from an acetabular ball, having:
   a first handle having a femoral engagement component at one end thereof,
   a second handle having an acetabular engagement component at one end thereof,
   a pivot pin interconnecting the first handle and the second handle;
   and/or, having:
   B) two or more bell elements and two or more jaw elements,
   each bell element having a correspondingly dimensioned jaw element, wherein
   a selected bell element and correspondingly dimensioned jaw element are adapted to work in coordination to extract an acetabular ball of a particular size from an acetabular cup, and wherein
   each individual jaw element is mounted on a shaft to form a jaw shaft, wherein
   each correspondingly dimensioned bell element and jaw element are configurable such that the jaw element is engageable about an acetabular ball of an acetabular cup, such that, in use, movement of a selected jaw shaft engages the selected correspondingly dimensioned bell element against the jaw element of the selected jaw shaft when an acetabular ball is removed from an acetabular cup.

2. The surgical tray apparatus and components of claim 1, further comprising a tool configured for removal of the implanted acetabular cup from an acetabulum, wherein said tool includes a shaft mountable to an extractor cup which is configured to be placed in contact against an acetabular ball of an implanted acetabular cup.

3. The surgical tray apparatus and components of claim 1, wherein in tool for separating a femoral cup from an acetabular ball, the femoral engagement component is rotatably connected to the first handle.

4. The surgical tray apparatus and components of claim 1, wherein in the tool for separating a femoral cup from an acetabular ball, the second handle includes a hinge which provides pivoting of a portion of the second handle located between the pivot pin and the acetabular engagement component.

5. The surgical tray apparatus and components of claim 1, wherein in the tool for separating a femoral cup from an acetabular ball, the acetabular engagement component includes an acetabular engagement ring pivotally connected to a distal end of the second handle.

6. The surgical tray apparatus and components of claim 5, wherein the acetabular engagement ring includes a tab extending outwardly therefrom configured to be retained within an indent present in a part of the second handle proximate to the acetabular engagement ring.

7. The surgical tray apparatus and components of claim 1, wherein in the tool for separating a femoral cup from an acetabular ball,
   the femoral engagement component is rotatably connected to the first handle, and,
   the second handle includes a hinge which provides for pivoting of a portion of the second handle located between the pivot pin and the acetabular engagement component.

8. The surgical tray apparatus and components of claim 1, wherein in the tool for separating a femoral cup from an acetabular ball
   the femoral engagement component is rotatably connected to the first handle, and,
   the acetabular engagement component includes an acetabular engagement ring pivotally connected to a distal end of the second handle.

9. The surgical tray apparatus and components of claim 1, further comprising a threaded jaw shaft nut, wherein the jaw shaft includes a proximal threaded portion engageable with threads of the jaw shaft nut.

10. The surgical tray apparatus and components of claim 9, further comprising a hollow outer shaft having at one end a shaft nut, the jaw shaft engageable within the outer shaft, wherein one of the bell elements is engageable at one end of the outer shaft, and the threaded jaw shaft nut is engaged upon the proximal threaded portion whereby rotation of the threaded jaw shaft nut urges a bell element against one of the jaw elements when the jaw element is engaged about an acetabular ball of an implanted acetabular cup.

11. The surgical tray apparatus and components of claim 1, further comprising:
   a femoral cup extractor having a shaft connected to a forked wedge via a connector at a distal end thereof, and a handle.

12. The surgical tray apparatus and components of claim 1, further comprising;
   a surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
  a shaft;
  an extractor cup affixed at its proximal end to a distal end of the shaft, the extractor cup having at its distal end a concave surface sized to articulate on the acetabular ball; and
  a blade having a proximal end affixed to the shaft and a distal portion sized to move adjacent or in close proximity to a convex surface of the acetabular cup, the convex surface of the acetabular cup being in contact with the acetabulum; and,
a detachable driver wrench adapted to affix the extractor cup to the shaft.

13. The surgical tray apparatus and components of claim 12, further comprising: a lever arm movably positioned in the shaft and adapted to facilitate rotation of the tool while maintaining downward pressure on the tool.

14. The surgical tray apparatus and components of claim 1, further comprising;
  a surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
  a shaft;
  an extractor cup concentrically affixed at its proximal end to a distal end of the shaft, with the extractor cup having at its distal end a concave surface sized to articulate on the acetabular ball;
  a blade having a proximal end affixed to the shaft and a distal portion sized to move adjacent or in close proximity to a convex surface of the acetabular cup, the convex surface of the acetabular cup being in contact with the acetabulum; and,
  a detachable driver wrench adapted to affix the extractor cup to the shaft.

15. The surgical tray apparatus and components of claim 14, wherein the extractor cup is mounted onto distal end of the shaft with a snap fit fitting.

16. The surgical tray apparatus and components of claim 14, wherein the extractor cup is mounted onto the distal end of the shaft with a threaded fitting.

17. The surgical tray apparatus and components of claim 1, further comprising:
  a surgical tool adapted for removing an acetabular cup from an acetabulum wherein the acetabular cup is a component of a reverse hip prosthesis and comprises an acetabular ball affixed to a stem which extends from a concave surface of the acetabular cup, the surgical tool comprising:
  a handle having a shaft and a moveable lever arm which facilitates rotation of the shaft while maintaining downward pressure on an extractor cup which is affixed at its proximal end to a distal end of the shaft, with the extractor cup having at its distal end a concave surface sized to articulate on the acetabular ball; and
  a blade having a proximal end affixed to the shaft and a distal portion sized to move adjacent or in close proximity to a convex surface of the acetabular cup, the convex surface of the acetabular cup being in contact with the acetabulum; and
  detachable driver wrench adapted to affix the extractor cup to the shaft.

18. The surgical tray apparatus and components of claim 17, wherein the extractor cup is mounted onto distal end of the shaft with a snap fit fitting.

19. The surgical tray apparatus and components of claim 18, wherein the extractor cup is mounted onto the distal end of the shaft with a threaded fitting.

20. A surgical method of using the tools from the surgical tray apparatus and components of claim 1, comprising the steps of:
  first selecting a joint separator, then separating the femoral cup from the acetabular ball, and
  thereafter, in any order, the further steps of:
  removing the femoral cup from the femoral implant and selecting an appropriately sized acetabular ball extractor based upon the size of the acetabular ball and removing the acetabular ball from the acetabular cup.

* * * * *